(12) United States Patent
Chu et al.

(10) Patent No.: US 11,925,315 B2
(45) Date of Patent: Mar. 12, 2024

(54) FLEXIBLE URETEROSCOPE WITH QUICK MEDICAL DEVICE ACCESS AND EXCHANGE

(71) Applicant: BOSTON SCIENTIFIC SCIMED, INC., Maple Grove, MN (US)

(72) Inventors: Michael S. H. Chu, Brookline, MA (US); Mayur Kiran Patel, Framingham, MA (US); Sacha Tang, Lowell, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 285 days.

(21) Appl. No.: 16/821,575

(22) Filed: Mar. 17, 2020

(65) Prior Publication Data

US 2020/0337529 A1 Oct. 29, 2020

Related U.S. Application Data

(60) Provisional application No. 62/837,340, filed on Apr. 23, 2019.

(51) Int. Cl.
*A61B 1/00* (2006.01)
*A61B 1/01* (2006.01)
(Continued)

(52) U.S. Cl.
CPC ...... *A61B 1/00098* (2013.01); *A61B 1/00066* (2013.01); *A61B 1/00094* (2013.01);
(Continued)

(58) Field of Classification Search
CPC ............ A61B 1/00066; A61B 1/00071; A61B 1/00096; A61B 1/00098; A61B 1/00135;
(Continued)

(56) References Cited

U.S. PATENT DOCUMENTS

| 6,053,860 A | 4/2000 | Brooks |
| 9,566,126 B2 | 2/2017 | Weltzner et al. |

(Continued)

FOREIGN PATENT DOCUMENTS

CN 101627894 A 1/2010

OTHER PUBLICATIONS

Office Action in Chinese Application No. 202080016307.4, dated Nov. 8, 2023 (10 pages).

*Primary Examiner* — Aaron B Fairchild
*Assistant Examiner* — Julianna J Nicolaus
(74) *Attorney, Agent, or Firm* — Bookoff McAndrews, PLLC

(57) ABSTRACT

A scope device includes a shaft, a deflectable portion, and a handle portion. The shaft is inserted through a body lumen to a target area within a body. The shaft defines first and second lumens extending along a proximal portion thereof. The first and second lumens are merged to form a common lumen along a distal portion thereof via a fitting having a structure which, when connected to the first and second lumens, converge the first and second lumens toward the common lumen. The deflectable portion is connected to the distal end of the shaft and includes a channel aligned with and in communication with the common lumen. The handle portion includes a connector having a first hub including a first channel open to and in communication with the first lumen and a second hub including a second channel open to and in communication with the second lumen.

12 Claims, 7 Drawing Sheets

(51) Int. Cl.
*A61B 1/307* (2006.01)
*A61B 18/22* (2006.01)

(52) U.S. Cl.
CPC ............ *A61B 1/00096* (2013.01); *A61B 1/01*
(2013.01); *A61B 1/307* (2013.01); *A61B 18/22*
(2013.01)

(58) Field of Classification Search
CPC ......... A61B 1/012; A61B 1/015; A61B 1/018;
A61B 2018/00166; A61B 2018/00511;
A61B 2018/00517
See application file for complete search history.

(56) References Cited

U.S. PATENT DOCUMENTS

| | | | |
|---|---|---|---|
| 2007/0088326 | A1 | 4/2007 | Kennedy, II |
| 2011/0213300 | A1* | 9/2011 | McWeeney .......... A61B 1/0052 |
| | | | 604/95.04 |
| 2015/0065807 | A1* | 3/2015 | Greenberg ............. A61B 1/307 |
| | | | 600/207 |
| 2017/0007345 | A1* | 1/2017 | Smith .................... A61B 1/018 |
| 2017/0303891 | A1* | 10/2017 | Yamashita .......... B29C 48/0018 |
| 2018/0235441 | A1* | 8/2018 | Huang ............... A61B 1/00135 |
| 2018/0289249 | A1 | 10/2018 | Harrah et al. |
| 2019/0282073 | A1* | 9/2019 | Truckai .................. A61B 1/051 |
| 2020/0000317 | A1* | 1/2020 | Cooper .................. A61B 34/71 |

* cited by examiner

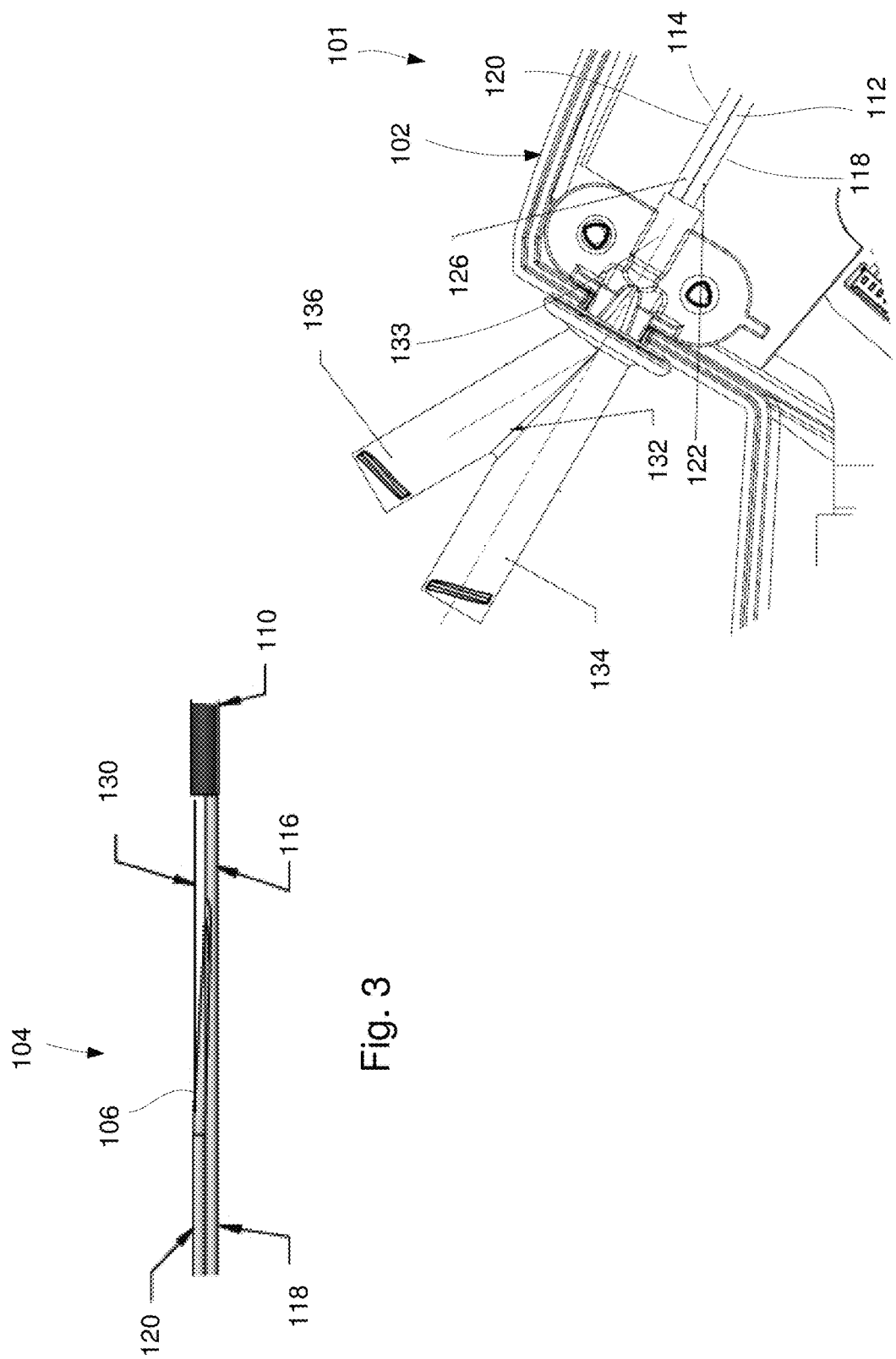

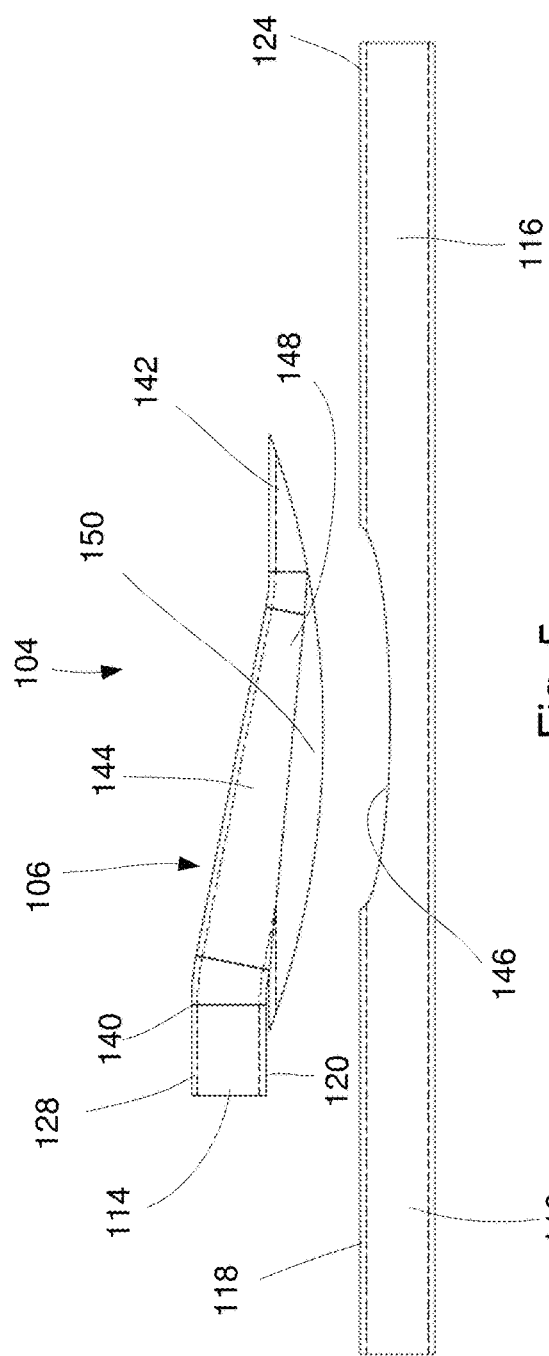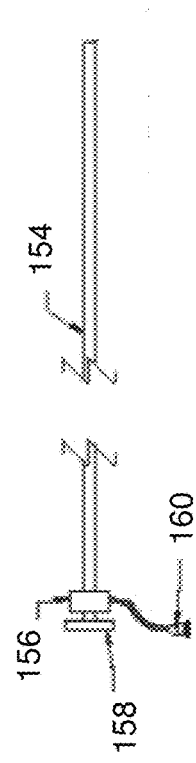

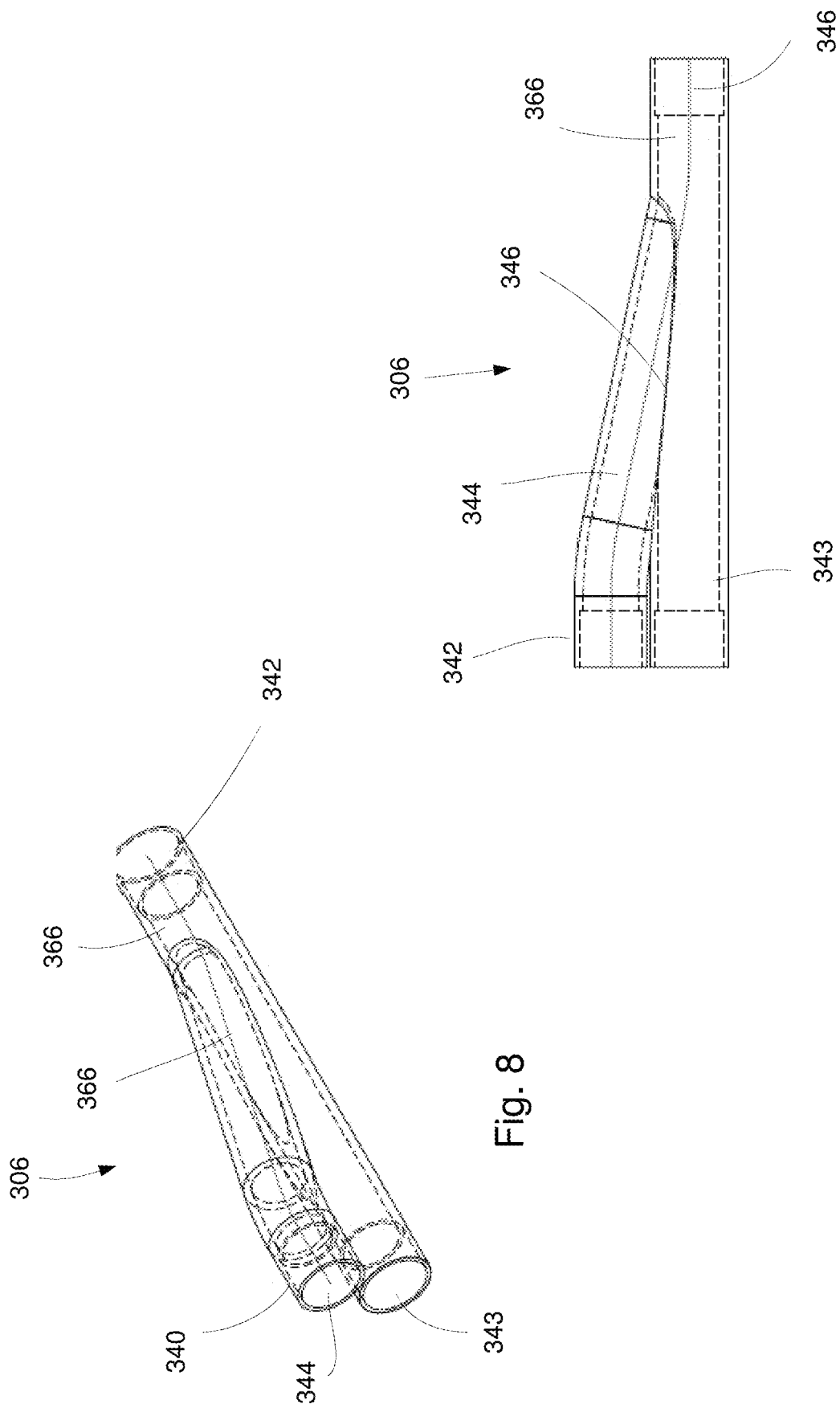

FLEXIBLE URETEROSCOPE WITH QUICK MEDICAL DEVICE ACCESS AND EXCHANGE

PRIORITY CLAIM

The disclosure claims priority to U.S. Provisional Patent Application Ser. No. 62/837,340 filed Apr. 23, 2019; the disclosure of which is incorporated herewith by reference.

BACKGROUND

Flexible ureteroscopes are often used in the examination of kidneys and, in particular, may be used in the treatment of kidney and ureteral stones. Ureteroscopes are typically used in conjunction with other devices such as, for example, guidewires, retrieval devices and laser fibers. As an example, urologists often use flexible ureteroscopes in combination with a laser or pneumatic impactor to fragment kidney stones and a basket to retrieve fragmented stones from the body. According to another example in which a dusting technique is utilized, urologists may use low-pulse, high-frequency laser energies of more powerful laser systems to pulverize stones into extremely fine fragments so that the fragments may be left behind in the kidney. These fine fragments may be passed spontaneously in the urine, potentially obviating the need for basket extraction and the use of ureteral access sheaths.

The consequences of residual stone fragments, however, remain controversial. Some urologists believe that all fragments, no matter how small, should be removed from the body. Stone dust in the lower pole of the kidney, for example, may not drain or pass out spontaneously. Thus, urologists will relocate the lower pole stones to the upper pole via a basket prior to dusting. Although dusting is an efficient method for dealing with stones, some stones are not good candidates for the dusting procedure. Dusting has proven to be very effective for mixed calcium, calcium phosphate, and uric acid stones, but may not be appropriate for harder stones such as calcium oxalate monohydrate stones. In addition, dusting has been shown to work well for stones in the 900 to 1100 Hounsfield unit range, but is less effective for stones in the 1400 to 1500 Hounsfield unit range. Thus, to manage and treat stones effectively, a ureteroscope must be used in conjunction with multiple devices, which are exchanged throughout the urologic procedure. During the exchange, however, the device can be damaged or contaminated by inadvertent drops to a non-sterile field such as the floor of the operating room.

SUMMARY

The present disclosure relates to a scope device, comprising a shaft sized and shaped to be inserted through a body lumen to a target area within a body and extending longitudinally from a proximal end to a distal end, the shaft defining a first lumen and a second lumen extending along a proximal portion thereof. The first and second lumens merge to form a common lumen along a distal portion thereof via a fitting having a structure which, when connected to the first and second lumens, converge the first and second lumens toward the common lumen. The scope device also comprises a deflectable portion connected to the distal end of the shaft and including a channel aligned with and in communication with the common lumen, the deflectable portion including a camera at a distal end thereof for visualizing the target area, and a handle portion connected to the proximal end of the shaft so that, in an operative configuration, the handle portion remains outside of the body, the handle portion including a connector having a first hub and a second hub, the first hub including a first channel open to and in communication with the first lumen so that a first medical device is insertable through the first hub to the first lumen to treat the target area, the second hub including a second channel open to and in communication with the second lumen so that a second medical device is insertable therethrough to the second lumen to the treat the target area.

In an embodiment, the first and second lumens may be defined via a first tubular member and a second tubular member, respectively.

In an embodiment, the first tubular member may include an opening extending laterally through a wall thereof, a portion of the first tubular member proximal of the opening defining the first lumen and a portion of the first tubular member distal of the opening defining the common lumen.

In an embodiment, the fitting may extend from a first end connected to the a distal end of the second tubular member to a second end and including a channel extending therethrough, a distal opening of the channel sized and shaped to correspond to the opening of the first tubular member so that, when the fitting is adhered thereto, the second lumen is open to and in communication with the common lumen via the channel of the fitting.

In an embodiment, the first tubular member may include an infusion channel extending longitudinally through the wall thereof, the infusion channel configured to receive a flow of fluid therethrough.

In an embodiment, the fitting may taper from a first end and toward a second end, a proximal portion of the fitting defining a first channel and a second channel which converge toward a common channel along a distal portion thereof so that, when the first and second tubular members are connected to the first channel and the second channel, respectively, each of the first and second lumens are open to and in communication with the common lumen via the common channel.

In an embodiment, the fitting may taper from a first end configured receive distal ends of the first and second tubular member toward a second end, the fitting defining a tapering channel extending therethrough from the first end to the second end so that, when the fitting is connected to the first and second tubular members, the first and second lumens are in communication with the common lumen via the tapering channel.

In an embodiment, the first and second lumens may extend within a tubular member extruded to include dual lumens.

In an embodiment, the fitting may extend from a first end including a coupling for connected to a distal end of the tubular member to a second end, a channel extending through the fitting from the first end to the second end, a distal portion of the fitting defining the common lumen, the distal portion of the fitting connected to the coupling via a tapered portion.

In an embodiment, a cross-sectional area of the tubular member may be substantially ovoid and a cross-sectional area of the common lumen is substantially circular such that the tapered portion tapers from a substantially ovoid shape to a circular shape.

In an embodiment, the fitting may be attached to at least one of the first and second lumens via one of an adhesive, melt liner and heat shrink.

In an embodiment, the fitting may be integrally formed with one of the first and second lumens.

The present disclosure also relates to a system for treating a target area accessible via a body lumen, comprising a scope device including a shaft sized and shaped to be inserted through the body lumen to a target area within a body and extending longitudinally from a proximal end to a distal end, the shaft defining a first lumen and a second lumen extending along a proximal portion thereof. The first and second lumens are merged to form a common lumen along a distal portion thereof via a fitting having a structure which, when connected to the first and second lumens, converge the first and second lumens toward the common lumen. A distal end of the common lumen is connected to a deflectable portion including a channel extending longitudinally therethrough such that the common lumen is aligned with and in communication with the channel of the deflectable portion, the deflectable portion includes a camera at a distal end thereof for visualizing the target area. The system also comprises a sheath configured to be assembled with the shaft such that the shaft extends longitudinally within a channel of the sheath, a proximal end of the sheath sealed about a proximal end of the shaft such that a fluid is deliverable to the target area via a space between an interior wall of the sheath and an exterior wall of the shaft.

In an embodiment, the first and second lumens may be defined via a first tubular member and a second tubular member, respectively.

In an embodiment, the first tubular member may include an opening extending laterally through a wall thereof, a portion of the first tubular member proximal of the opening defining the first lumen and a portion of the first tubular member distal of the opening defining the common lumen, the fitting extends from a first end connected to the a distal end of the second tubular member to a second end and including a channel extending therethrough, a distal opening of the channel sized and shaped to correspond to the opening of the first tubular member so that, when the fitting is adhered thereto, the second lumen is open to and in communication with the common lumen via the channel of the fitting.

The present disclosure also relates to a method for treating ureteral or kidney stones comprising inserting a scope device to a target stone within a target area of a body by sliding the scope device along a guidewire that has been inserted to the target area via a body lumen, removing the guidewire from the scope device, inserting a laser fiber through a first lumen and a common lumen along a shaft of the scope device to the target stone, applying a laser energy to the target stone via the laser fiber to one of fragment and pulverize the target stone, and removing fragmented portions of the stone via a second lumen and the common lumen; wherein the first lumen and the second lumen merge toward the common lumen which extends along a distal portion of the shaft, each of the first lumen and the second lumen being open to and in communication with the common lumen.

BRIEF DESCRIPTION

FIG. 3 shows an enlarged longitudinal side view of a distal portion of the scope device of FIG. 1;

FIG. 4 shows an enlarged side view of a Y-connector attached to a handle portion of the scope device of FIG. 1;

FIG. 5 shows a transparent longitudinal side view of a fitting of the scope device of FIG. 1, which merges first and second lumens of a shaft toward a single common lumen along a distal portion thereof;

FIG. 6 shows a longitudinal side view of a sheath according to an exemplary embodiment of the system of FIG. 1;

FIG. 8 shows a transparent perspective view of a fitting of a scope device according to an alternate embodiment of the present disclosure;

FIG. 9 shows a transparent longitudinal side view of the fitting of FIG. 8;

DETAILED DESCRIPTION

Figure 1:
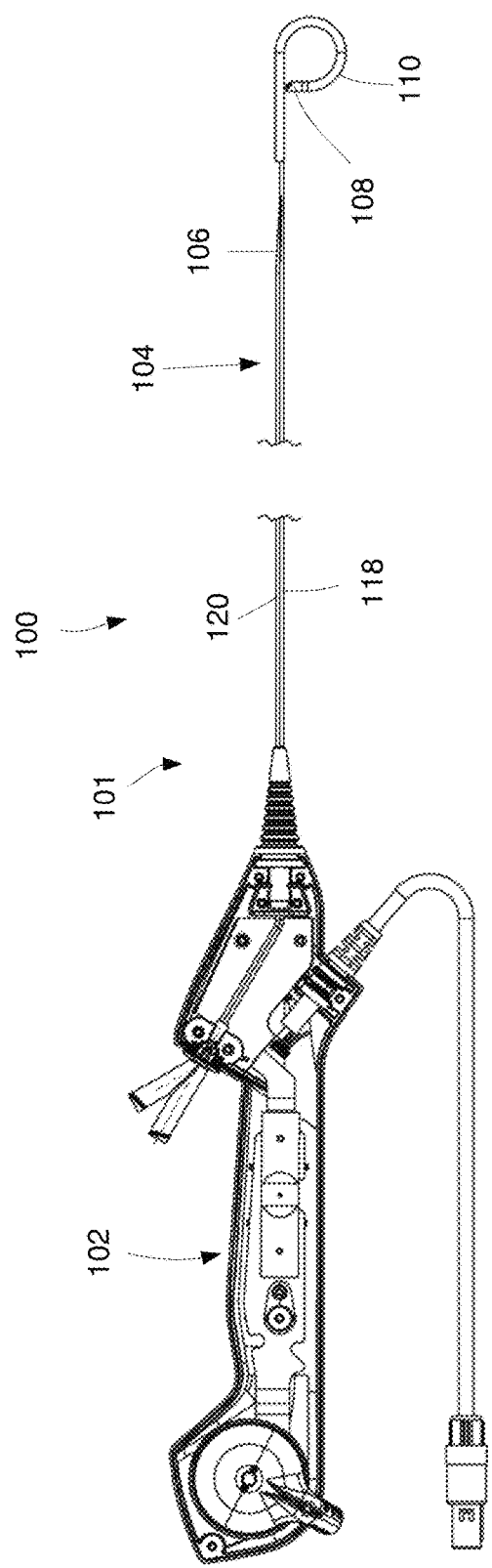
FIG. 1 shows a longitudinal side view of system comprising a scope device according to an exemplary of the present disclosure.
Figure 2:
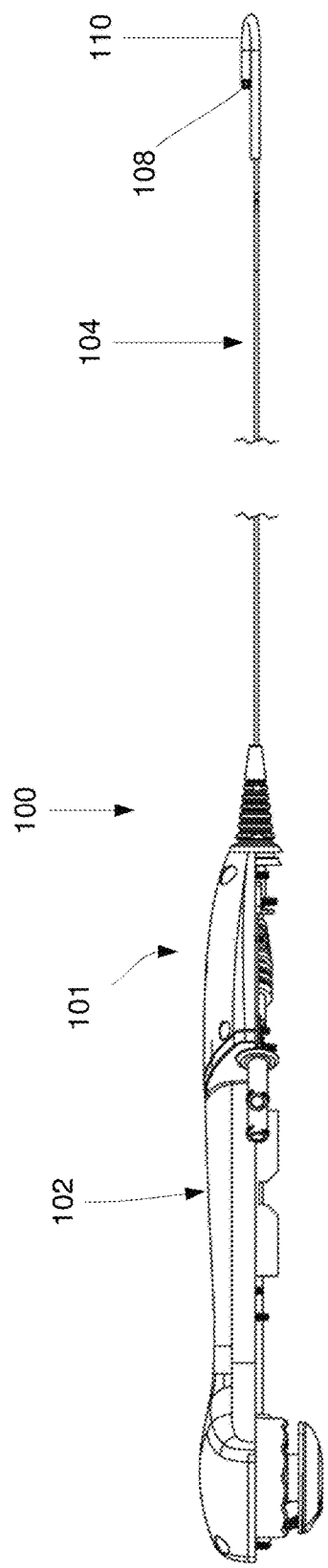
FIG. 2 shows another longitudinal side view of the scope device of FIG. 1, rotated 90 degrees about a longitudinal axis thereof.

The present disclosure may be further understood with reference to the following description and appended drawings, wherein like elements are referred to with the same reference numerals. The present disclosure relates to systems and methods for accessing, examining and/or treating a hollow organ or cavity of a body and, in particular, may relate to systems and method for performing ureteroscopies. The exemplary embodiments describe a system including a ureteroscope which may be used for treating ureteral and/or kidney stones. The exemplary ureteroscope includes a dual lumen working channel which merges into a single common lumen toward a distal end thereof to accommodate multiple medical devices (e.g., guidewires, retrieval devices, laser fibers, etc.) that may need to be exchanged during a urologic procedure.

As would be understood by those skilled in the art, a dual lumen extending along an entire length of a shaft of a ureteroscope would require a larger outer diameter along a distal portion thereof, resulting in reduced deflection range and reduced visual image quality. A single common lumen along the distal portion of the ureteroscope, however, maintains the deflection and image quality of current single lumen scopes such as, for example, the LithoVue™. The merging of the dual lumens into the single common lumen also provides quick device exchange with internal storage to prevent inadvertent mishaps.

For example, a medical device may be quickly evacuated from the common single lumen to provide a channel via which suction may be provided to quickly unclog stone dust, tissue or debris. In another example, a medical device may be parked in each of the dual lumens, leaving the common single lumen clear so that either of the parked medical devices may be quickly and sequentially deployed, withdrawn and exchanged through the common lumen without requiring a medical device to be entirely removed from the scope. Although the exemplary embodiments specifically describe a ureteroscope for treating ureteral or kidney stones, it will be understood by those of skill in the art that the system of the present disclosure may be adapted for other purposes such as, for example, tissue biopsy retrieval. For example, the scope device may be adapted to receive a biopsy device and snare or other retrieval device. It should be noted that the terms "proximal" and "distal", as used herein, are intended to refer to a direction toward (proximal) and away from (distal) a user of the device (e.g., physician).

As shown in FIGS. 1-6, a system 100 according to an exemplary embodiment of the present disclosure comprises a scope device 101 (e.g., ureteroscope) including a flexible shaft 104 configured to be inserted through a body lumen to a target area (e.g., ureter, kidney accessed via a natural body orifice) and a handle member 102 which, when the shaft 104 is inserted into the body lumen, remains outside of the body. The shaft 104 extends distally from the handle member 102 to a deflectable portion 110. The shaft 104 includes a first lumen 112 and a second lumen 114 which merge into a single common lumen 116 along a distal portion thereof via a fitting 106, which will be described in further detail below.

The scope device 101 also includes pull wires and electric cables 130 extending along a length thereof for facilitating a deflection of the deflectable portion 110 and imaging via a camera (not shown) at a distal end 108 of the deflectable portion 110. The deflectable portion 110 includes a channel extending therethrough in alignment with the common lumen 116 so that medical devices inserted through the common lumen 116 may be passed through the deflectable portion 110 and distally out of the shaft 104 where they can be visualized via the camera. Elements of the shaft 104— e.g., the first lumen 112, the second lumen 114 and the pull wires and electric cables 130—may be adhered to one another or held together via, for example, an oversheath extending along a length thereof.

As would be understood by those skilled in the art, the handle member 102 of this embodiment may include features for actuating and/or controlling the deflectable portion 110 and the camera. The scope device 101 may also comprises a Y-connector 132 attached to the handle member 102, the Y-connector 132 including a first hub 134 and a second hub 136 via which the first and second lumens 112, 114 may be accessed, respectively. The system 100 may comprise other medical devices configured to be inserted through the scope device 101 such as, for example, a guidewire, a laser fiber and a retrieval device. The system 100 may also comprise an access sheath 154, as shown in FIG. 6, providing a working channel for the scope device 101.

The first and second lumens 112, 114 of the shaft 104 may be configured in any of a variety of ways. In one embodiment, each of the first and second lumens 112, 114 is defined via substantially separate tubular components—a first tubular member 118 and a second tubular member 120, respectively. The first tubular member 112 extends from a proximal end 122 attached to the handle member 102 to a distal end 124. Similarly, the second tubular member 114 extends from a proximal end 126 attached to the handle member 102 to a distal end 128. The first and second lumens 112, 114 of the first and second tubular members 118, 120 may be merged to form the common lumen 116 via a fitting 106 which, as will be described in greater detail below, may have any of a number of different configurations. A cross-sectional area of the first and second tubular members 118, 120 may have any of a variety of shapes and sizes. For example, the cross-sectional areas of the first and second tubular members 118, 120 may be substantially circular or oval. In addition, each of the first and second tubular members 118, 120 may have the same or varying interior and/or outer diameters depending upon an application thereof. The first and second tubular members 118, 120 may be reinforced with a coil or a braid.

As shown in FIG. 4, the Y-connector 132 may be attached to the handle member 102 such that the Y-connector is connected to the proximal ends 122, 126 of the first and second tubular members 118, 120, respectively. In particular, the proximal ends 122, 126 in this embodiment are received within a distal portion 133 of the Y-connector 132. As described above, the Y-connector 132 includes first and second hubs 134, 136. The first hub 134 and the second hub 136, which extend proximally from the handle member 102, converge toward the distal portion 133. The first hub 134 is connected to the first tubular member 118 such that a medical device inserted through the first hub 134 passes into the first lumen 112. The second hub 136 is connected to the second tubular member 120 such that a medical device inserted into the second hub 13 passes into the second lumen 114.

The channel of the first hub 134 is in communication with the first tubular member 118 and the channel of the second hub 136 is in communication with the second tubular member 120. The first and second hubs 134, 136 in this embodiment are configured as connectors such as, for example, medical luer connectors. The first and second hubs 134, 136 may be angled relative to one another. In one particular embodiment, a longitudinal axis of the first hub 134 is substantially aligned with a longitudinal axis of the distal portion 133 of the Y-connector 132 while a longitudinal axis of the second 136 is angled relative thereto.

As described above, the first and second lumens 112, 114 of the first and second tubular members 118, 120 merge into the common lumen 116 via the fitting 106. In one embodiment, as shown in FIG. 5, the common lumen 116 extends along a distal portion of the first tubular member 118 while the first lumen 112 extends along a proximal portion thereof such that the distal end 124 of the first tubular member 118 is connected to the deflectable portion 110. The second tubular member 120, through which the second lumen 114 extends, merges with the first tubular member 118 via the fitting 106. In this embodiment, the fitting 106 extends distally from the second tubular member 120 and is attached to an opening 146 extending laterally through the first tubular member 118. The opening 146 may, for example, be a skived elongated opening extending along a portion of a length of the first tubular member 118 as would be understood by those skilled in the art.

The fitting 106 extends from a first end 140 attached to the distal end 128 of the second tubular member 120 to a second end 142 and includes a channel 144 extending therethrough from the first end 140 to the second end 142. The fitting 106, in this embodiment, is integrally formed with the second tubular member 120 or, in another embodiment, is attached thereto via, for example, an adhesive. A distal opening 148 of the channel 144 at the second end 142 of the channel 144 substantially corresponds in size and shape to the opening 146 of the first tubular member 118 so that the second end 142 of the fitting 106 may be adhered thereto to form a fluid-tight enclosure therewith. The fitting 106 in this embodiment is configured to correspond to an outer profile of the first tubular member 118 and, in one embodiment, includes a flange 150 extending from opposing sides of the distal opening 148 of the channel 144 of the fitting 106 such that the flange 150 extends over a perimeter of the skived opening 146 of the first tubular member 118. The flange 150 may be adhered to the opening 146 using an adhesive such as, for example, glue.

The channel 144 of the fitting 106 is sloped toward the first tubular member 118 from the first end 140 to the second end 142 so that, when a medical device (e.g., guidewire, laser fiber, retrieval device) is inserted distally through the second lumen 114 and into the fitting 106, a distal end of the medical device slides along the sloped surface 126 and is guided into the common lumen 116 extending along the distal portion of the first tubular member 118. Thus, the second channel 114 is open to and in communication with the common lumen 116 via the channel 144 of the fitting 106 such that the common lumen 116 extends distally of the opening 146 while the first lumen 112 extends proximally of the opening 146.

As described above, the scope device 101 may be utilized with other medical devices such as, for example, laser fibers, guidewires and retrieval devices. In addition, the scope device 101 may be used in conjunction with a sheath, through which the scope device 101 may be inserted to the target area. In one embodiment, the scope device 101 may be utilized with a thin-walled sheath 154, which has an inner diameter slightly larger than an outer diameter of the shaft 104 of the scope device 101 so that, fluid (e.g., saline) may flow through a space between the shaft 104 and the sheath 154 to the target area. The thin-walled sheath 154 may be sealed against a proximal end of the shaft 104 to prevent a proximal flow of the fluid through the space. The sheath may be sealed to the shaft 104 of the scope device 101 via, for example, a Tuohy-Borst adapter 156 including a cap 158 for tightening the adapter 156 about the shaft 104. The adapter 156 in this embodiment also includes a side port 160, through which fluid may be injected. The thin-walled sheath 154 reduce trauma to areas surrounding traversed by the device (e.g., ureter) as compared to a conventional sheath having a thicker wall, and may be supported by the shaft 104 during introduction into the body lumen.

A Tuohy-Borst adapter may also be used to seal and secure other devices to the scope device 101. For example, the scope device 101 may include a Tuohy-Borst adapter attached to the first huh 134 so that when a medical device (e.g., laser fiber) is inserted therein and secured thereto, fluid may be injected and/or a suction force may be applied about the medical device. Markings such as, for example, ring markings on the medical device proximal of the hub 1 may be used so that a user may get an indication of a position of a distal end of the medical device relative to the fitting 106 of the scope device 101.

According to an exemplary method for treating, for example, a kidney stone using the system 100, a guidewire is inserted along a urethra, through the bladder and along a ureter to the target area in which the kidney stone is located via fluoroscopic guidance. In one embodiment, a conventional access sheath may be inserted into the body lumen along the guidewire so that the scope device 101 may be inserted therethrough to the target area. In another embodiment, the thin-walled sheath 154 may be assembled with the shaft 104 of the scope device 101 by securing and sealing a proximal end of the sheath 154 to the proximal end of the shaft 104 via the adapter 156. The assembled system 100 may then be slid along the guidewire to the target area by receiving the guidewire within the common lumen 116 and the first lumen 112 and sliding the assembled system 100 therealong.

Once the scope device 101 has reached the target area, the guidewire may be removed from the body and the stone may be examined via the camera at the distal end 108 of the deflectable portion 110. The deflectable portion 110 may be deflected, as necessary, to best capture imaging of the stone. A retrieval device such as, for example, a basket retrieval device, may be inserted through the first hub 134 to the first lumen 112 and the common lumen 116 to remove the stone from the body or to reposition the stone for easier manipulation and fragmentation. In one example, the kidney stone may be moved from an area in the lower pole to the upper pole. When the stone has been repositioned for fragmentation, the retrieval device may be withdrawn from the common lumen 116 to a "parked" position in which a distal end thereof is just proximal of a proximal end of the common lumen 116 so that a path from the second lumen 114 to the common lumen 116 is open and/or clear. A laser fiber may then be inserted through the second lumen 114 and common lumen 116 via the second hub 136 so that the laser fiber may fragment and/or pulverize the stone.

In one embodiment, the user may elect to fragment the stone so that the fragmented portions may be removed via, for example, basket retrieval. In particular, upon fragmentation of the stone, the laser fiber may be withdrawn to a "parked" position in which a distal end thereof is just proximal of the proximal end of the common lumen 116 so that the retrieval device may be moved distally through the common lumen 116 and extended distally therefrom to grasp a fragmented portion of the stone. If the portions of the fragmented stone are still too large to be removed via the access sheath or through the ureter, the parked laser may be quickly exchanged for the retrieval device to further fragment the stone.

Another quick exchange with the retrieval device will enable removal of the fragmented portion. As will be understood by those of skill in the art, the retrieval device holds the fragmented portion of the stone distally of the distal end 108 of the scope device 101 so that the scope device 101 must be removed from the body to remove the fragmented portion of the stone from the body. Thus, the above-described process may be repeated, as necessary, for each fragmented portion of the stone. It will also be understood by those of skill in the art, that the user may elect to utilize a conventional sheath in this embodiment so that, when the scope device 101 is removed from the body, the access sheath remains in position so that the scope device 101 may be easily reinserted to the target area via the access sheath to remove another fragmented portion of the stone.

In another embodiment, the user may elect to dust or pulverize the stone into fine fragments which may be suctioned from the body. Upon dusting of the stone, the laser fiber may be moved to the parked position and the retrieval device removed from the first lumen 112, so that the dust fragments may be suctioned therefrom via the first lumen 112. Fluid may be provided via the space between the sheath 154 and the shaft 104 to replenish any fluid suctioned out during this process. If necessary, the parked laser fiber may be quickly deployed to further fragment any stone fragments. In addition, the parked laser fiber may be moved distally into the common lumen to unclog the common lumen 116 from any larger sized stone fragments.

If so desired, the basket retrieval process may be combined with the dusting procedure. For example, any larger fragments that have not been removed via suction may be subsequently removed via basket retrieval. Upon removal of the fragmented portions of the stone, the system 100 may be removed from the body. As described above, although the exemplary embodiments are described with respect to a ureteroscope for treating ureteral or kidney stones, the scope device 100 of the present disclosure may be similarly configured for other procedures including, for example, tissue biopsy. In this embodiment, the scope device 100 may be used in conjunction with medical devices such as, for example guidewires, biopsy devices and retrieval devices (e.g., snare).

Figure 7:
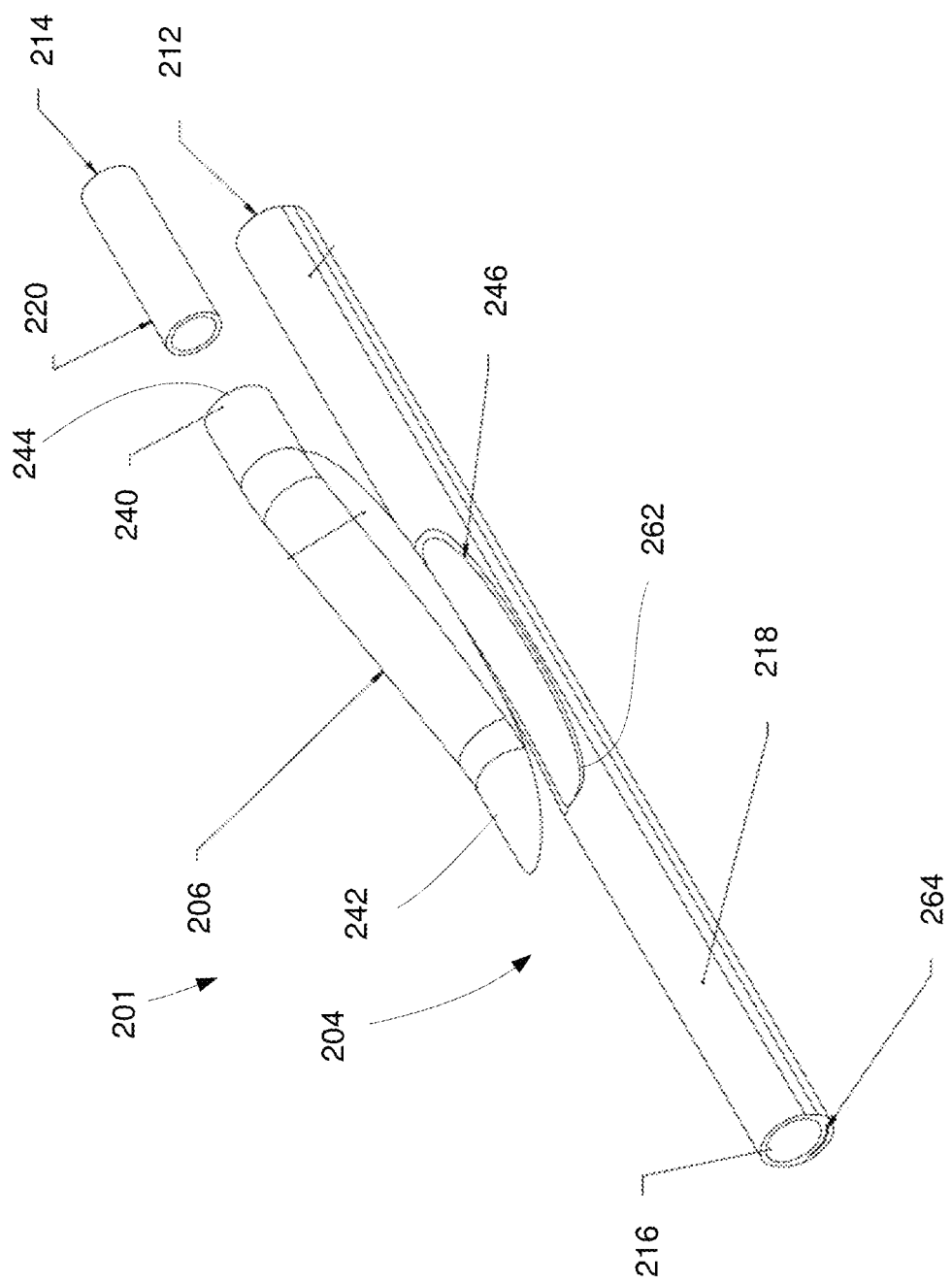
FIG. 7 shows an exploded perspective view of a portion of a scope device according to another exemplary embodiment of the system of FIG. 1.

As shown in FIG. 7, a scope device 201 according to another exemplary embodiment is substantially similar to the scope device 101, comprising a shaft 204 including a first lumen 212 and a second lumen 214 which are merged to form a single common lumen 216 along a distal portion of the shaft 204 via a fitting 206. The fitting 206 in this embodiment is also substantially similar to the fitting 106, the fitting 206 merging a first tubular member 118 defining the first lumen 212 with a second tubular member 220 defining the second lumen 214 to form the single common lumen 216 along the distal portion of a shaft 204. Similarly to the scope device 101, the first tubular member includes an opening 246 extending laterally through a wall 262 of the first tubular member 218 so that a portion of the first tubular member 218 proximal of the opening 246 defines the first lumen 212 while a portion of the first tubular member 212 distal of the opening 246 defines the common lumen 216. Similarly to the fitting 106, the fitting 206 extends from a proximal end 240 attached to the distal end 228 of the second tubular member to a second end 242 secured about the opening 246 of the first tubular member 218. A channel 244 extends through the fitting 206 from the first end 240 to the second end 242 so that the second lumen 214 of the second tubular member 220 is open to and in communication with the common lumen 216 via the fitting 206.

The first tubular member 218, however, further includes a longitudinal channel 264 extending through the wall 262 along a length thereof. The channel 264 is configured to deliver infusion fluids to the target area so that fluid is not required to be inserted through an access sheath. For example, for a scope device 201 utilized in a dusting procedure, fluid may be delivered to the target area via the channel 264 so that fluid is not required to be delivered via a sheath (e.g., the thin-walled sheath 154). Thus, the scope device 201 may be inserted to the target area without the use of a sheath. Although the scope device 201 is not required to be assembled with or inserted through a sheath, the scope device 201 and may be used in substantially the same manner as the scope device 101, as described above with respect to the system 100.

As described above, the first and second lumens 112, 114 may be merged toward a single common lumen via a fitting having any of a variety of configurations. As shown in FIGS. 8 and 9, a fitting 306 according to an alternate embodiment similarly merges the first lumen 112 and the second lumen 114, as described with respect to the scope device 101, toward the common lumen 116. The fitting 306, however, tapers from a first end 340 toward a second end 342 and defines a first channel 343 and a second channel 344 therein, which are merged toward a single common channel 366 toward the distal end 342. The second channel 344 in this embodiment is sloped toward the first channel 343 to merge therewith via an opening 346 extending therebetween. Thus, proximal of the opening 346, the first and second channels 343, 344 are separate from one another.

In this embodiment, distal ends 124 and 128 of the first and second tubular members 118, 120 are configured to be received within the first and second channels 343, 344, respectively, of the fitting 306 so that the first tubular member 118 is open to and in communication with the first channel 343 and the second tubular member 120 is open to and in communication with the second channel 344. A third tubular member (not shown) defining the common lumen 116 is configured to be received within the single channel 366 at the distal end 342 so that each of the first and second tubular members 118, 120 are open to and in communication with the third tubular structure via the channel 366. The third tubular member may extend distally from the fitting 306 to be connected to the deflectable portion 110. In another embodiment, the distal end 342 of the fitting 306 may be connected directly to the deflectable portion 110 so that the single channel 366 forms the common lumen for each of the first and second tubular members 118, 120.

Figure 11:
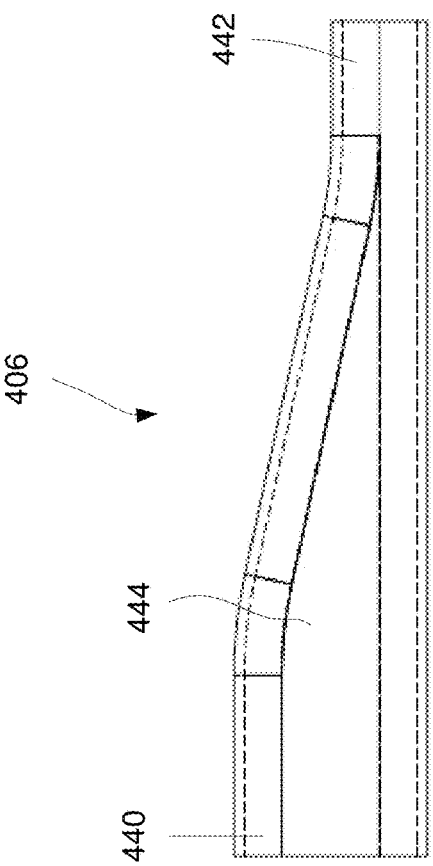
FIG. 11 shows a transparent longitudinal side view of the fitting of FIG. 10.
Figure 10:
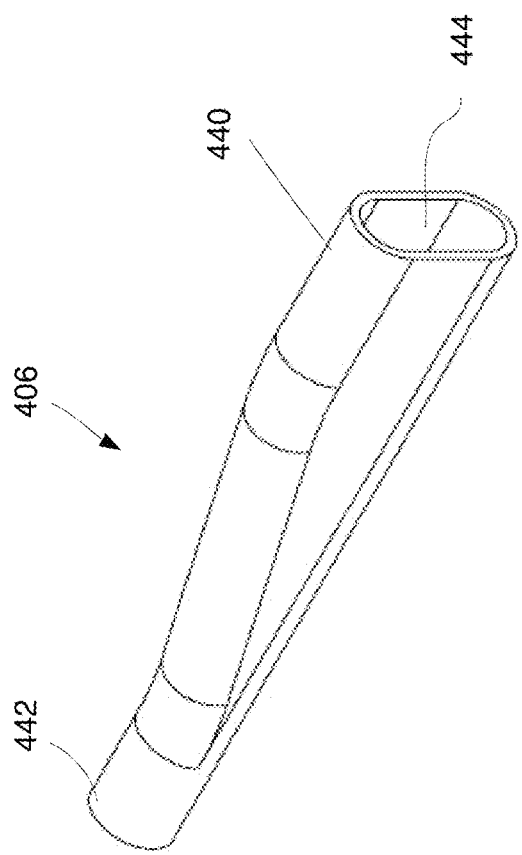
FIG. 10 shows perspective view of a fitting of a scope device according to yet another alternate embodiment of the present disclosure.

As shown in FIGS. 10 and 11, a fitting 406 according to yet another alternate embodiment is substantially similar to the fitting 306 described above, extending from a first end 440 to a second end 442. Rather than defining two distinct channels which merge to a single channel toward the second end 442, however, the fitting 406 includes one channel 444 which tapers from the first end 440 toward the second end 442. The first end 440 is configured to receive the distal ends 124, 128 of the first and second tubular members 118, 120. The second end 442 is configured to receive a third tubular member (not shown) defining the common lumen 116 or, in another embodiment, a distal portion 466 of the channel 444 defines the common lumen. Thus, when the first and second tubular members 118, 120 are coupled to the fitting 406, both the first and second lumens 112, 114 are open to and in communication with the channel 444. In one embodiment, a cross-section of the channel 444 at the first end 440 is substantially ovoid so that the distal ends 124, 128 of the first and second tubular member 118, 120 may be received therein, while a cross-section of the channel 444 at the second end 442 is substantially circular. It will be understood by those of skill in the art, however, that the channel 444 may have any of a variety of shapes and sizes so long as the channel 440 is sufficiently tapered to prevent any interference with the deflectable portion 110 and/or the camera at the distal end 108 thereof.

Figure 12:
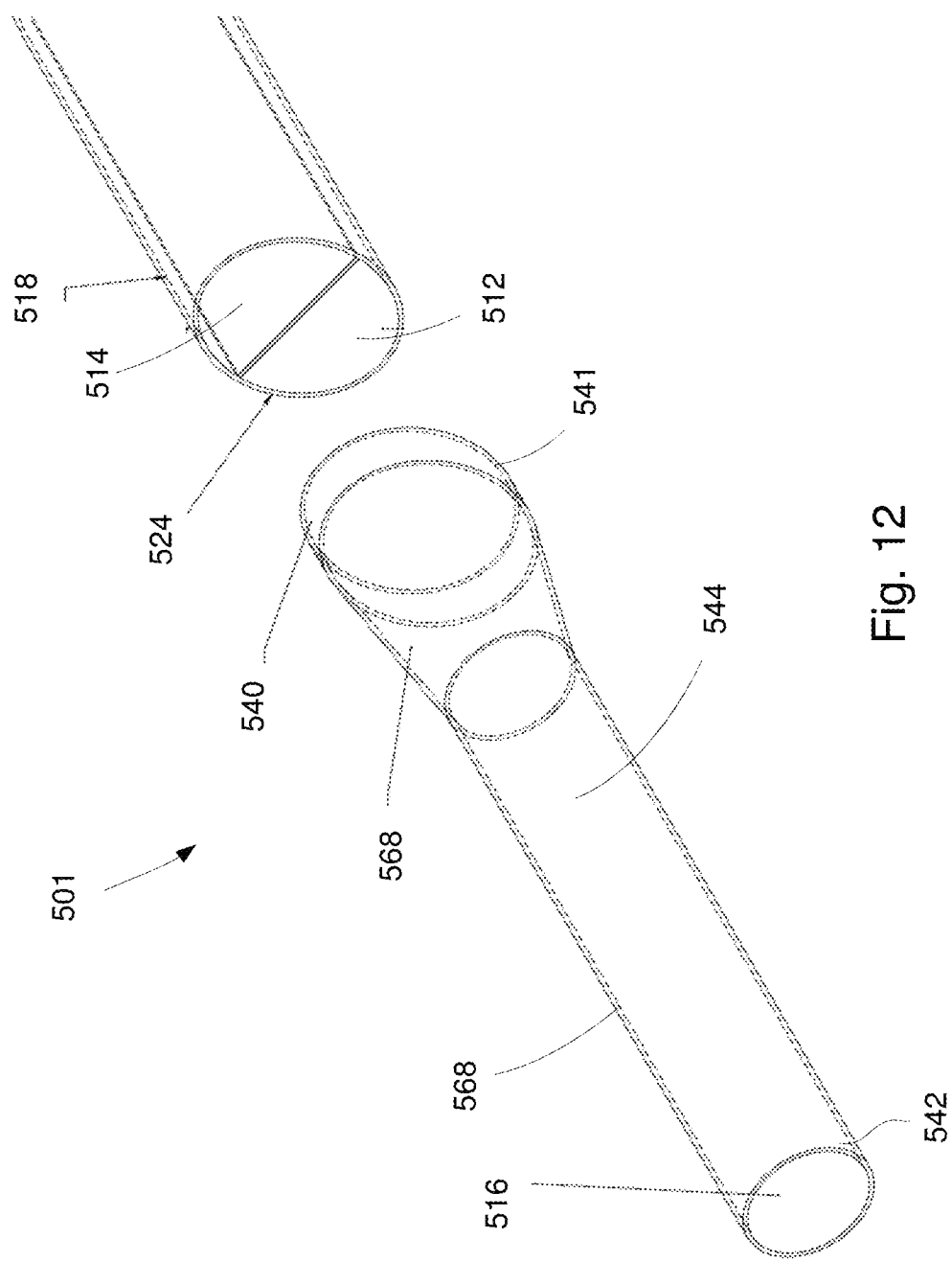
FIG. 12 shows an exploded perspective view of a portion of a scope device according to another exemplary embodiment of the present disclosure.

As shown in FIG. 12, a scope device 501 according to another exemplary embodiment is substantially similar to the scope device 101 described above with respect to the system 100, comprising a shaft 504 including first and second lumens 512, 514 which are merged toward a single common lumen 516 along a distal portion thereof via, for example, a fitting 506. Rather than two distinct tubular members defining the first and second lumens 512, 514, however, the shaft 504 may be comprised of a single tubular member 518 extruded to include a dual lumen—the first lumen 512 and the second lumen 514. In one embodiment, the tubular member 518 may include an ovoid cross-section such that each of the first and second lumens 512, 514 have a substantially D-shaped cross-section. It will be understood by those of skill in the art, however, that the tubular member 518 may have any of a variety of shapes and sizes so long as the tubular member 518 includes the first and second lumens 512, 514 having a size and shape suitable for their intended purpose. For example, each of the first and second lumens 512, 514 may be configured to receive medical devices such as, for example, a guidewire, a laser fiber and/or a retrieval device.

The fitting 506 extends from a first end 540 to a second end 542 and includes a channel 544 extending therethrough. The fitting 506 of this embodiment includes a coupling portion 541 at the first end 540 for coupling the fitting 506 to the tubular member 518 and a distal portion 566 defining the common lumen 516. The coupling portion 541 of the first end 542 may, for example, have an ovoid cross-sectional area that is slightly larger than the distal end 542 so that the distal end 524 may be received therein. It will be understood by those of skill in the art, however, that the coupling portion 541 may be coupled to the tubular member 518 in any of a number of different manners. The distal portion 566 may be connected to the coupling portion 541 via a tapered portion 568 which tapers from the ovoid cross-section of the first end to a substantially circular cross-section corresponding to a desired cross-sectional area of the common lumen 516. Thus, when the fitting 506 is coupled to the tubular member 518, each of the first and second lumens 512, 514 is open to and in communication with the channel 544 and the common lumen 516 so that devices inserted through either of the first and second lumens 512, 514 may be similarly inserted into the common lumen 516, as described above with respect to the system 100. The fitting 506 may be adhered to the tubular member 518 or formed integrally therewith.

Each of the fittings 106-506 described may be adhered to a corresponding one of the tubular members via an adhesive such as, for example glue. Alternatively or in addition, the fittings 106-506 may be comprised of and/or adhered to relevant portions of the shafts 104-504 via a melt liner, heat shrink and/or other adhesive. It will be understood by those of skill in the art that scope devices including the fittings 206-506 may be used in substantially the same manner as the scope device 101 described above with respect to the system 100.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiment disclosed, but rather modifications are also covered within the scope of the present invention as defined by the appended claims.

What is claimed is:

1. A scope device, comprising:
    a shaft extending longitudinally from a proximal end to a distal end, the shaft being sized and shaped to be inserted through a body lumen to a target area within a body, the shaft including a first lumen defined by a first tubular member of the shaft and a second lumen extending along a proximal portion thereof, the first and second lumens merged to form a common lumen along a distal portion thereof via a fitting having a structure which, when connected to the first and second lumens, converges the first and second lumens toward the common lumen, the fitting including a flange extending from opposing sides of a distal opening of a channel that extends through the fitting, wherein the first tubular member having has an opening through a wall thereof and wherein the fitting is attached to the opening such that the flange extends over a perimeter of the opening;
    a deflectable portion connected to the distal end of the shaft and including a channel aligned with and in communication with the common lumen, the deflectable portion including a camera at a distal end thereof for visualizing the target area; and
    a handle portion connected to the proximal end of the shaft so that, in an operative configuration, the handle portion remains outside of the body, the handle portion including a connector having a first hub and a second hub, the first hub including a first channel open to and in communication with the first lumen so that a first medical device is insertable through the first hub to the first lumen to treat the target area, the second hub including a second channel open to and in communication with the second lumen so that a second medical device is insertable therethrough to the second lumen to the treat the target area.

2. The scope device of claim 1, wherein the first and second lumens are defined via the first tubular member and a second tubular member, respectively.

3. The scope device of claim 2, wherein the first tubular member includes an opening extending laterally through a wall thereof, a portion of the first tubular member proximal of the opening defining the first lumen and a portion of the first tubular member distal of the opening defining the common lumen.

4. The scope device of claim 3, wherein the fitting extends from a first end connected to a distal end of the second tubular member to a second end, the second tubular member including a channel extending therethrough, a distal opening of the channel sized and shaped to correspond to the opening of the first tubular member so that, when the fitting is adhered thereto, the second lumen is open to and in communication with the common lumen via the channel of the fitting.

5. The scope device of claim 3, wherein the first tubular member includes an infusion channel extending longitudinally through the wall thereof, the infusion channel configured to receive a flow of fluid therethrough.

6. The scope device of claim 2, wherein the fitting tapers from a first end and toward a second end, a proximal portion of the fitting defining a first channel and a second channel which converge toward a common channel along a distal portion thereof so that, when the first and second tubular members are connected to the first channel and the second channel, respectively, each of the first and second lumens are open to and in communication with the common lumen via the common channel.

7. The scope device of claim 2, wherein the fitting tapers from a first end configured to receive distal ends of the first and second tubular members toward a second end, the fitting defining a tapering channel extending therethrough from the first end to the second end so that, when the fitting is connected to the first and second tubular members, the first and second lumens are in communication with the common lumen via the tapering channel.

8. The scope device of claim 1, wherein the first and second lumens extend within a tubular member extruded to include dual lumens.

9. The scope device of claim 8, wherein the fitting extends from a first end including a coupling for connecting to a distal end of the tubular member to a second end, a channel extending through the fitting from the first end to the second end, a distal portion of the fitting defining the common lumen, the distal portion of the fitting connected to the coupling via a tapered portion of the fitting.

10. The scope device of claim 9, wherein a cross-sectional area of the tubular member is substantially ovoid and a cross-sectional area of the common lumen is substantially circular such that the tapered portion tapers from a substantially ovoid shape to a circular shape.

11. The scope device of claim 1, wherein the fitting is attached to at least one of the first and second lumens via one of an adhesive, melt liner and heat shrink.

12. The scope device of claim 1, wherein the fitting is integrally formed with one of the first and second lumens.

* * * * *